United States Patent [19]

Weiss et al.

[11] Patent Number: 4,942,182

[45] Date of Patent: Jul. 17, 1990

[54] TREATMENT FOR COCAINE ADDICTION

[76] Inventors: Susan R. B. Weiss, 4522 Chestnut St., Bethesda, Md. 20814; Robert M. Post, 3510 Turner La., Chevy Chase, Md. 20815; Thomas G. Aigner, 5900 Ryland Dr., Bethesda, Md. 20817

[21] Appl. No.: 317,405

[22] Filed: Mar. 1, 1989

[51] Int. Cl.$^5$ ............................................. A61K 27/00
[52] U.S. Cl. ...................................... 514/812; 424/10

[58] Field of Search ........................... 424/10; 514/812

Primary Examiner—Stanley J. Friedman

[57] ABSTRACT

Chronic oral adminstration of carbamazepine may be used to block reinforcing effects and toxic effects of cocaine. It is preferred that the subject be esstentially "clean" of codeine at the time the treatment with carbamazepine is commenced.

6 Claims, No Drawings

TREATMENT FOR COCAINE ADDICTION

This invention provides a means of treating cocaine addiction by chronic oral administration of carbamazepine. While it had previously been reported that administration of carbamazepine would prevent epileptic and lidocaine-induced seizures, the use of this medication to overcome toxic and habituating action of cocaine had not previously been known.

BACKGROUND OF THE INVENTION

Cocaine abuse has become a major public health problem in recent years as more reinforcing forms of the drug have become available. Acute intoxication from cocaine is marked by convulsions and cardiac arrhythmias, and chronic cocaine use can be associated with increasing behavioral pathology and toxicity. The mechanisms underlying the reinforcing and toxic effects of cocaine are not fully understood, particularly since cocaine has dual actions as a potentiator of catecholaminergic systems; in particular, the dopamine system, and as a local anesthetic. Although dopaminergic antagonists have shown some success in blocking the reinforcing effects of cocaine in experimental animals, there is, at present, no pharmacological treatment that is efficacious and acceptable to patients. Carbamazepine is a major antiepileptic drug that has also been shown to be effective in the treatment of manic-depressive disorder. Recent studies in the Biological Psychiatry Branch have shown that chronic carbamazepine is extremely effective in preventing cocaine-induced seizures and deaths in rats.

Carbamazepine is an iminostilbene derivative that is used clinically to treat seizure disorders, trigeminal neuralgia, and, most recently, manicdepressive illness. Carbamazepine is very effective as an anticonvulsant in several experimental seizure paradigms including amygdala kindling, alcohol withdrawal, and maximal electroconvulsive shock, but is less effective on seizures induced by pentylenetetrazole and high-dose picrotoxin. The effectiveness of anticonvulsants has been shown to depend upon the stage of evolution of the seizure process. For example, carbamazepine suppresses completed amygdala-kindled seizures in rats, but is ineffective in preventing their development. While diazepam inhibits the early development and fully-kindled phases of amygdala kindling, it is not effective in the later phase of kindling when seizures occur spontaneously. Conversely, phenytoin shows the opposite profile on amygdala-kindled seizures—it is ineffective in early stages, but blocks spontaneous seizures.

Lidocaine is a local anesthetic that can be used to kindle seizures when given repeatedly in large, but initially subconvulsant, doses. This process has been called pharmacological kindling. Local anesthetic seizures resemble those produced by electrical kindling of the amygdala in that there is a prominent facial component, clonic jerking of the forepaws, and electroencephalographic evidence of seizure activity in the amygdala. In addition, the lidocaine seizures have been shown to increase glucose utilization in the amygdala, hippocampus, and perirhinal cortex. Cocaine is equipotent to lidocaine as a local anesthetic, but additionally has psychomotor stimulant properties that are thought to result from its ability to block catecholamine reuptake. Repeated administration of low to moderate doses of cocaine induces increased motor activation and stereotypy, a process called behavioral sensitization or reverse tolerance. This aspect of cocaine's effect appears closely related to its psychomotor stimulant properties, as similar behavioral changes are not seen with repeated lidocaine administration, but are observed with other psychomotor stimulants; e.g., amphetamine. Repeated administration of high doses of cocaine results in the progressive development of seizures which follow a time course akin to kindling.

In a study at the National Institute of Mental Health, it was found that chronic oral treatment with carbamazepine inhibited the development of lidocaine- and cocaine-kindled seizures in the rat. The carbamazepine diet produces combined blood levels of carbamazepine and its -10,11-epoxide that are similar to those achieved in humans treated with carbamazepine for affective, pain, or seizure disorders.

DESCRIPTION OF THE INVENTION

It is the purpose of this invention to provide a method for treating cocaine addiction by chronic administration of carbamazepine to block reinforcing effects of cocaine.

It is, furthermore, a purpose of this invention to provide a method of blocking toxic effects of intermittent administration of cocaine by chronic administration of carbamazepine.

It has now been determined that, in addition to its use as an anticonvulsant for prevention of seizures, the chronic use of carbamazepine is an appropriate method for treatment of habituation by blocking reinforcing properties of cocaine and for relief of toxic responses to cocaine such as panic attacks. To effect the desired result, the carbamazepine must be administered chronically to maintain a relatively constant blood level. Doses ranging from 200-2000 mg/day will usually result in a blood level of 4-12 $\mu$g/ml. The drug must be given when the patient is relatively drug free. This is because the use of carbamazepine appears at times to worsen seizures and increase lethal effects of cocaine when given acutely near the time cocaine is administered.

While the preferred method of treatment is by oral administration, any method which would result in a relatively constant blood level of the compound would be acceptable. The pharmaceutical compositions for administration may contain therein the usual fillers known in the pharmaceutical art.

Since the reinforcing effects of cocaine are so powerful, the cocaine user becomes addicted rapidly. The addiction is persistent, and even the user who is aware of the often lethal results of cocaine dosing may be unable to resist the reinforcing effects of cocaine. The chronic oral administration of carbamazepine provides a useful adjuct to other means of treating the cocaine addict.

We claim:

1. A method of blocking toxic effects of cocaine comprising the chronic administration of carbamazepine to a host susceptible to cocaine addiction in an amount sufficient to achieve a 4 0 12 ug/ml blood concentration of carbamazepine.

2. A method of claim 1 wherein the carbamazepine is given orally.

3. A method of claim 2 wherein the dosage of carbamazepine given is 200-2000 mg/day.

4. A method of blocking the reinforcing effects of cocaine by administering to a susceptible host a reinforcing-blocking effective amount of carbamazepine.

5. A method of claim 4 wherein the carbamazepine is given by oral route in a pharmaceutically acceptable carrier.

6. A method of claim 5 wherein the dosage of carbamazepine administered is 200-2000 mg/day.

* * * * *

UNITED STATES PATENT AND TRADEMARK OFFICE
CERTIFICATE OF CORRECTION

PATENT NO. : 4,942,182

DATED : July 17, 1990

INVENTOR(S) : Susan R.B. Weiss

It is certified that error appears in the above-identified patent and that said Letters Patent is hereby corrected as shown below:

| | |
|---|---|
| Cover page inventors addresses | Delete "4522 Chestnut St." and substitute --5816 Kingswood Rd.-- Delete "3510" and substitute --3502-- |
| Abstract | Delete "esstentially" and substitute --essentially-- Delete "codeine" and substitute --cocaine-- |
| Col. 2, line 26 | Delete "habituation" and substitute --addiction-- |
| Col. 2, line 28 | Add --and seizures.-- after "attacks" |
| Col. 2, line 32 | Delete "The drug" and substitute --Carbamazepine-- |
| Col. 2, line 33 | Delete "drug" and substitute --cocaine-- |
| Col. 2, line 49 | Delete "adjuct" and substitute --adjunct-- |
| Col. 2, line 55 | Delete "4012" and substitute --4-12-- |

Signed and Sealed this

Fourth Day of August, 1992

Attest:

DOUGLAS B. COMER

*Attesting Officer*   *Acting Commissioner of Patents and Trademarks*